(12) United States Patent
Bellaton et al.

(10) Patent No.: US 10,436,562 B2
(45) Date of Patent: Oct. 8, 2019

(54) SURFACE MEASUREMENT PROBE

(71) Applicant: ANTON PARR TRITEC SA, Peseux (CH)

(72) Inventors: Bertrand Bellaton, Neuchâtel (CH); Marcello Conte, Neuchâtel (CH)

(73) Assignee: ANTON PAAR TRITEC SA, Peseux (CH)

(*) Notice: Subject to any disclaimer, the term of this patent is extended or adjusted under 35 U.S.C. 154(b) by 144 days.

(21) Appl. No.: 15/522,127

(22) PCT Filed: Nov. 2, 2015

(86) PCT No.: PCT/EP2015/075491
§ 371 (c)(1),
(2) Date: Apr. 26, 2017

(87) PCT Pub. No.: WO2016/071296
PCT Pub. Date: May 12, 2016

(65) Prior Publication Data
US 2017/0336188 A1  Nov. 23, 2017

(30) Foreign Application Priority Data
Nov. 3, 2014 (EP) .................................... 14191442

(51) Int. Cl.
G01B 3/22 (2006.01)
G01Q 30/10 (2010.01)
(Continued)

(52) U.S. Cl.
CPC ................. G01B 3/22 (2013.01); G01N 3/42 (2013.01); G01Q 30/10 (2013.01); G01Q 60/366 (2013.01);
(Continued)

(58) Field of Classification Search
CPC .... G01B 3/22; G01N 3/42; G01N 2203/0226; G01N 2203/0286; G01Q 30/10; G01Q 60/366
(Continued)

(56) References Cited

U.S. PATENT DOCUMENTS 5,084,981 A * 2/1992 McMurtry ............. G01B 7/012
                                                                33/1 D
5,365,673 A * 11/1994 Haimer ................... G01B 5/012
                                                                33/503
(Continued)

FOREIGN PATENT DOCUMENTS

GB         1214864        12/1970
GB         2494467         3/2013

Primary Examiner — Justin Seo
Assistant Examiner — Tania C Courson
(74) Attorney, Agent, or Firm — Duane Morris LLP; Gregory M. Lefkowitz; Jason M. Nolan

(57) ABSTRACT

Surface measurement probe comprising:
  a hollow probe body extending along a longitudinal axis and comprising a proximal end adapted to be mounted to a test apparatus and a distal end;
  a retaining arrangement situated inside the probe body and extending along said longitudinal axis, the retaining arrangement being arranged to maintain the surface measurement probe in an assembled state;
  a probe tip supported at the distal end of the probe body and arranged to contact a sample;
  a bead situated inside the probe body and interposed between the probe tip and the retaining arrangement, the bead comprising a thermally-insulating material.

20 Claims, 5 Drawing Sheets

(51) Int. Cl.
*G01Q 60/36* (2010.01)
*G01N 3/42* (2006.01)

(52) U.S. Cl.
CPC ............... *G01N 2203/0226* (2013.01); *G01N 2203/0286* (2013.01)

(58) Field of Classification Search
USPC .................................................. 33/556, 559
See application file for complete search history.

(56) References Cited

U.S. PATENT DOCUMENTS

| | | | | |
|---|---|---|---|---|
| 7,228,641 | B2 * | 6/2007 | Hunter | F16C 17/08 33/556 |
| 9,829,417 | B2 * | 11/2017 | Schmitz | G01B 3/00 |
| 10,113,851 | B2 * | 10/2018 | Ooyama | G01B 5/0014 |
| 2006/0162176 | A1 * | 7/2006 | Lummes | G01B 3/008 33/556 |
| 2014/0326707 | A1 | 11/2014 | Schmitz | |
| 2017/0336308 | A1 * | 11/2017 | Bellaton | G01N 3/04 |

* cited by examiner

SURFACE MEASUREMENT PROBE

CROSS-REFERENCE TO RELATED APPLICATIONS

This application is a § 371 national stage entry of International Application No. PCT/EP2015/075491, filed Nov. 2, 2015, which claims priority to European Patent Application No. 14191442.4, filed Nov. 3, 2014, the entire contents of which is incorporated herein by reference.

TECHNICAL FIELD

The present invention relates to the field of surface testing of materials. More particularly, it relates to a surface measurement probe particularly suited for use in high-temperature environments.

STATE OF THE ART

Micro- and nanoindentation are commonly used to measure the mechanical properties of a particular material sample, typically with applications of very small forces in the mN and smaller range. Such measurements are often required to be carried out at elevated temperatures to investigate how materials behave at elevated temperatures at which the crystalline structure may be different, or a glass transition temperature may have been surpassed, or the melting temperature may be approaching. These high temperature measurements, which may be as high as 800° C. or even 1000° C., present particular challenges in respect of not only the effect of different coefficients of thermal expansion of the materials constituting the probe, but also in respect of temperature flows which occur if the tip temperature and the sample temperature differ. Contact between a hotter tip and a cooler sample, or vice-versa, results in thermal flows which change the temperature of the sample, and may result in thermal stresses causing dimensional changes due to the coefficient of thermal expansion of the tip and the sample. These changes negatively affect the measurement accuracy.

US 2011/252874 discloses a surface measurement probe for use in a hot testing environment. In order to minimize the influence of heat conduction and differing coefficients of thermal expansion, the tip holder is simply constructed of thermally-insulating material. Furthermore, various heating arrangements are provided in order to manipulate the temperature of the probe and to mitigate the above-mentioned problems. However, such measures are not sufficiently effective, and are unsatisfactory for use in an IR-bath-type heating arrangement such as disclosed in the co-pending application in the name of the present applicant and filed the same day.

GB 1 214 864 discloses a micro-hardness testing machine for testing hot samples. This machine comprises a long tubular probe, provided with an indenter tip at its distal end. A radiant heat dissipation system comprising radial fins is rigidly fixed around a mid-section of the tubular probe so as to radiate away heat being conducted along the probe, and these fins slide in a cooled block. Since the fins move within a cooled area, thermal stresses can be generated in the tubular probe, which is already very long and hence flimsy, and hence the precision of the measurements possible with this system are extremely limited.

Other prior art surface measurement probes are disclosed in documents WO 2013/074623 and GB 2494467.

An object of the invention is thus to overcome the above-mentioned drawbacks of the prior art, and thereby to propose a surface measurement probe with reduced thermal transmission.

DISCLOSURE OF THE INVENTION

This object is attained by a surface measurement probe comprising a hollow probe body extending along a longitudinal axis and comprising a proximal end adapted to be mounted to a test apparatus and a distal end, a retaining arrangement situated inside the probe body and extending along said longitudinal axis, and a probe tip supported at the distal end of the probe body and arranged to contact a sample in the conventional manner. The retaining arrangement is arranged to maintain the surface measurement probe in an assembled state and to maintain the various components correctly aligned with respect to one another. The probe further comprises a bead situated inside the probe body and interposed between the probe tip and the retaining arrangement, the bead comprising a thermally-insulating material. Further beads may also be provided, e.g. stacked along the axis of the probe body. Such a thermally-insulating material may for instance have a thermal conductivity less than 20 $Wm^{-1}k^{-1}$, preferably less than 10 $Wm^{-1}k^{-1}$, further preferably less than 2 $Wm^{-1}k^{-1}$ e.g. of a material such as Macor or another glass, ceramic or glass-ceramic. This bead acts as a thermal resistance to transmission of infrared radiation re-radiated inside the distal end of the probe, by means of absorbing and/or reflecting such infrared radiation, thereby limiting its transmission towards the proximal end of the probe.

Advantageously, the bead comprises a metallic coating, which may comprise at least one of gold, silver, aluminium, platinum, rhodium, ruthenium, palladium. This metallic coating has a high reflectivity for infrared radiation, and thus serves to reflect infrared radiation back towards the tip.

Advantageously, the bead is substantially spherical, minimising contact between the bead and the other components of the probe.

Advantageously, the retaining arrangement comprises a transverse pin secured to the distal element, e.g. by passing through corresponding openings in the wall of this latter. In a first variant, the retaining arrangement further comprises a core maintained in tension, e.g. by a tension screw, the transverse pin passing through a transverse hole in the core, with the bead in contact with the core. In a second variant, a retaining arrangement further comprises a tension spring attached to the transverse pin, with the bead in contact with the transverse pin. This tension spring can, at its other end, be connected e.g. to part of the proximal element, and be shaped so as to apply tension to the transverse pin and thereby to hold the components of the surface measurement probe together. Other arrangements are of course possible.

Advantageously, a bead positioning spring is provided, this bead positioning spring being situated between the bead and the probe tip, the bead positioning spring being arranged to act so as to position the bead against a corresponding part of the retaining arrangement, i.e. the core or the transverse pin as appropriate. The bead can thus be consistently positioned against the core, while minimizing thermal contact with the tip. Furthermore, the probe may comprise a thermocouple situated in thermal contact with the probe tip and positioned by said bead positioning spring, optionally via a button element positioned between the thermocouple and the bead positioning spring. The thermocouple is likewise well-supported in the probe, without the need for further fixing pieces.

The same aim of the invention is equally attained by a surface measurement probe comprising a tubular probe body extending along a longitudinal axis and comprising a proximal end adapted to be mounted to a test apparatus and a distal end, a retaining arrangement situated inside the probe body and extending along said longitudinal axis, the retaining arrangement being arranged to maintain the surface measurement probe in an assembled state, and a probe tip supported at the distal end of the probe body and arranged to contact a sample.

The probe body furthermore comprises a distal element situated at said distal end, a proximal element situated at said proximal end, and a thermal dissipation element situated between said distal end and said proximal end, and not around the probe body as in GB 1 214 864. This arrangement presents a significant resistance to conduction of heat from the distal element to the proximal element of the probe, much more so than simply arranging a thermally resistive element (such as an element of ceramic, Macor or similar) between the distal and proximal elements. This occurs since the thermal dissipation element promotes the sideways radiation of conducted heat which reaches it, reducing heat transmission to the proximal element by redirection of a proportion thereof, rather than simply by presenting an increased resistance to flow.

Advantageously, the thermal dissipation element is separated from at least one of the proximal element and the distal element by a respective spacer comprising a thermally-insulating material. Such a material may have a thermal conductivity of less than 20 $Wm^{-1}k^{-1}$, preferably less than 10 $Wm^{-1}k^{-1}$, further preferably less than 2 $Wm^{-1}k^{-1}$, such as quartz, a glass, a ceramic, or a glass-ceramic. Even greater thermal resistance is thus provided.

Advantageously, the retaining arrangement extends through at least part of the proximal element, the spacer, the thermal dissipation element and part of the distal element. The retaining arrangement can thus align and position the various elements.

Advantageously, the retaining arrangement comprises a transverse pin secured to the distal element. In a first variant, the retaining arrangement also comprises a core through which the transverse pin passes, the core being secured to the proximal element by a screw passing through a hole provided in the proximal element such that the core is maintained in tension. A particularly stable retention is thus attained, in which the various elements, spacers etc. are maintained in compression with a minimum of components. In a second variant, the retaining arrangement comprises a tension spring attached to the transverse pin and to the proximal element. This variant provides an extremely simple solution for retention which, due to the spring, can automatically absorb any thermal expansion of the surface measurement probe when it is heated.

Advantageously, the thermal dissipation element can be constructed integrally, i.e. as a single piece, with the proximal element. An extremely simple construction with a minimum of parts is thus possible.

Advantageously, the surface measurement probe comprises both the above-mentioned bead arrangement and the above-mentioned spacer arrangement.

BRIEF DESCRIPTION OF THE DRAWINGS

Further details of the invention will now be explained in reference to the following figures, in which.

EMBODIMENT OF THE INVENTION

Figure 1:
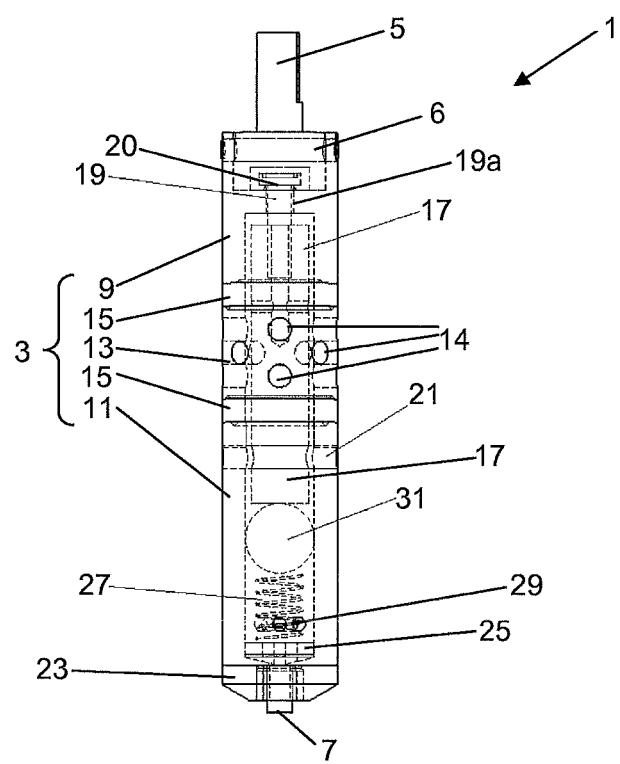
FIG. 1 shows a transparent view of a surface measurement probe according to the invention.
Figure 2:
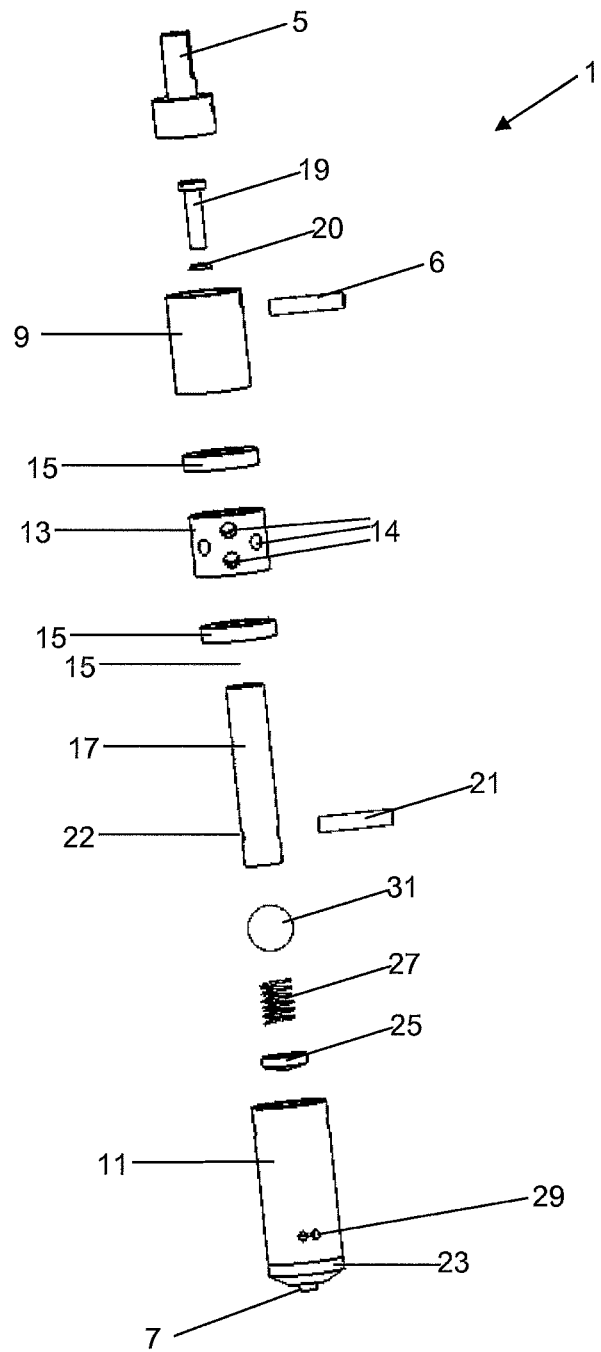
FIG. 2 shows an exploded view of the probe of FIG. 1.

FIGS. 1 and 2 illustrate a surface measurement probe 1 according to a first embodiment of the invention. The invention will first be described in reference to this first embodiment, further variants being described afterwards.

Surface measurement probe 1 comprises a probe body 3, formed generally as a hollow tube with closed ends, having a proximal end (situated towards the top of the figures), and a distal end (situated towards the bottom of the figures). The proximal end is adapted to interface with a test apparatus of any convenient type, for instance that described in EP 1 674 850 or EP 2 065 695, by means of mounting interface 5, which may be of any convenient form. Mounting interface 5 may be a separate piece as in FIGS. 1 and 2, or may be integral with another component of the probe body 3 as in FIGS. 3, 4, 5 and 6. Mounting interface 5 is advantageously constructed of a thermally insulating material such as Macor, produced by Corning. This material is a glass-ceramic comprising fluorphlogopite mica in a borosilicate glass matrix and has excellent thermal and mechanical properties, as well as good machinability. It has a very low thermal conductivity of substantially 1.46 $Wm^{-1}K^{-1}$. The distal end is the free end, and supports a probe tip 7, which may be a flat or rounded reference tip intended to serve as a reference for measuring a sample, or a pointed indentation tip intended to form an indentation in a sample upon application of an indentation force. Such tips 7, and suitable materials therefor such as hardened steel, diamond etc., are generally known in the art and need not be described further, and can be used not only for unidirectional indentation measurements, but also for tribological measurements in which the tip is drawn laterally across the surface of the sample, or bulk property measurements in which the indentation force is applied obliquely.

Probe body 3, in its simplest form, may be a simple, single piece tube of metal, ceramic, or other convenient material. However, in the present embodiment it comprises a proximal element 9, situated at the proximal end of the probe body 3, and a distal element 11, situated at the distal end of the probe body 3. Between the proximal end and the distal end of the probe 1, and more particularly between the proximal element 9 and the distal element 11, is a thermal dissipation element 13 separated from each of the proximal and distal elements 9, 11 via a spacer 15, of annular form, the function of which will be described below in more detail. Although a pair of spacers 15 situated either side of the thermal dissipation element 13 are illustrated in the embodiment of FIG. 1, it should be noted that it is sufficient that only one spacer 15 be used, ideally between the thermal dissipation element 13 and the proximal element 9, or even no spacers at all (see the embodiment of FIG. 4). Alternatively, a pair of adjacent spacers may be used on only one side of the thermal dissipation element 13. Other embodiments eliminate the spacers 15 entirely (see below). In all of these cases, the thermal dissipation element 13 is thus sandwiched between the proximal element 9 and the distal element 11.

Thermal dissipation element 13 serves to dissipate heat by radiation and may be e.g. of steel, molybdenum, suitable ceramics or similar, and may also be provided with lateral perforations 14. It may also be coloured black externally to promote radiation of heat, and/or may be coated internally with an infrared-reflective material such as gold, silver, platinum, rhodium, ruthenium, aluminium or platinum. Alternatively, thermal dissipation element 13 may be plain or comprise other structures such as ribs, flutes, rings etc. Spacers 15 may be of any convenient thermally insulating material, however as the invention is practised today quartz is used since it has low conductivity (approx. 6.8 to 12 $Wm^{-1}K^{-1}$) depending on crystal orientation) and is substantially transparent to infrared radiation, however suitable glasses or suitable ceramics may also be used.

The proximal element 9 and the distal element 11 may be of any convenient material such as molybdenum, macor, or another suitable ceramic, glass or glass-ceramic. Proximal element 9 may be attached to mounting interface 5 by means of upper transverse pin 6, e.g. of Macor or other glass, ceramic or glass-ceramic, which crosses the proximal element between two corresponding holes provided therein.

Figure 4:
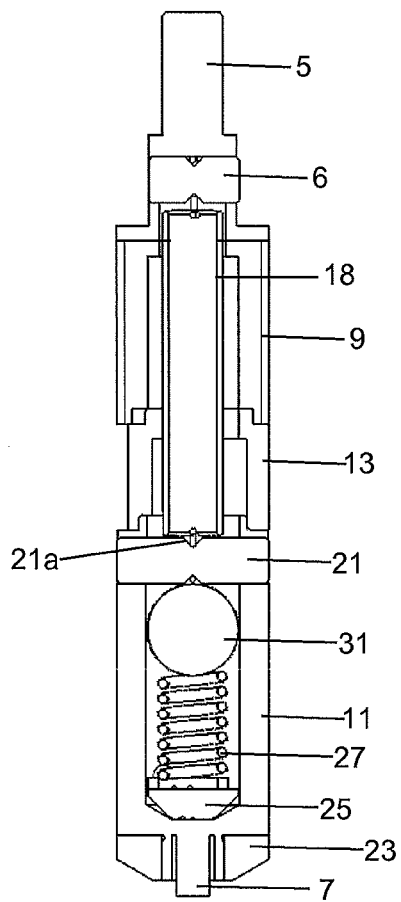
FIG. 4 shows a cross-section of a further variant of a probe according to the invention.
Figure 5:
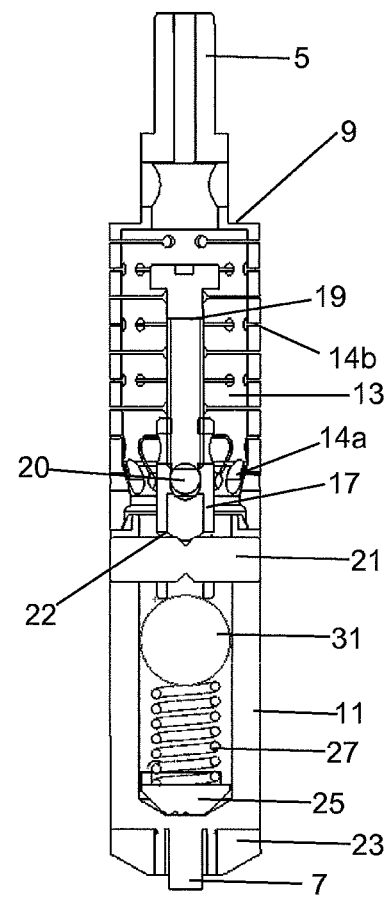
FIG. 5 shows a cross-section of a yet further variant of a probe according to the invention.
Figure 6:
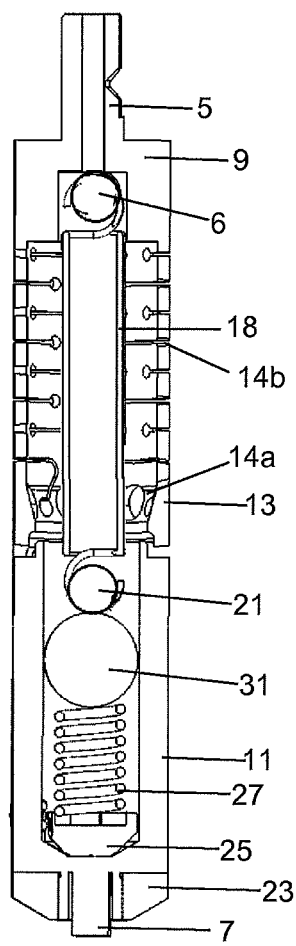
FIG. 6 shows a cross-section of a yet further variant of a probe according to the invention.

A core 17 of thermally insulating material, such as the above-mentioned Macor, passes from proximal element 9, in which it is secured by a screw 19 passing through a corresponding hole 19a in the proximal element, through sandwich structure 13, 15, and into distal element 11, in which it is secured by a transverse pin 21 which passes through a transverse hole 22 in the core 17 and a corresponding pair of transverse holes 22a passing through the sidewall of the distal element 11. Screw 19 is also associated with a resilient element 20, such as a spring washer as illustrated in the figures, so as to compensate some dilation of the various elements, and a clearance is provided between the core 17 and the proximal element 9 so as to permit thermal expansion to occur. Core 17 thus serves to align the elements of probe body 3, and to hold them together since tension applied by screw 19 is applied to distal element 11 via pin 21, thus supporting the sandwich structure 13, 15 in compression, the core 17 being maintained in tension. Core 17, pin 21 and screw 19 generically form a retaining arrangement adapted to retain the parts of the surface measurement probe in an adapted to maintain the surface measurement probe in an assembled state. The embodiments of FIGS. 4-6 illustrate different variants of retaining arrangements (see below), however other arrangements are possible, such as threaded rods, threading or welding the various elements together, or any other possible system for retaining the probe in an assembled state.

Tip 7 is rigidly supported in a tip body 23, rigidly attached to distal element 11. A thermocouple (not illustrated) is situated inside distal element 11, in thermal contact with tip 7, where it is held in place by a bead positioning spring 27 and an appropriately-shaped button element 25, which could be omitted if the thermocouple is appropriately shaped so as to be held in place without button element 25. Electrical connections (not illustrated) pass through lateral openings 29 is provided in the distal element 11, to enable the temperature of the tip 7 to be accurately measured.

Bead positioning spring 27 extends along the cavity inside the distal element 11, towards an end face of core 17. Situated between the bead positioning spring 27 and the end face of core 17 is a bead 31, i.e. at least one bead since two or more beads could clearly be stacked one on top of the other along the axis of the probe body 3.

Bead 31 is of thermally insulating material, such as a ceramic, and may also be coated in a metal such as gold, platinum, rhodium, ruthenium, palladium or similar. As the invention is practised today, the bead 31 is spherical, however other shapes are foreseeable such as ovoid.

The overall structure of the measurement probe 1 having now been described, the function of the various elements and their interactions will appear more clearly in the following.

Although the measurement probe 1 is perfectly suited to be used in a cool environment, or in a conventionally-heated environment (e.g. in which the sample and/or the tip 7 are heated by laser, induction, resistive heating and so on), it is particularly suited to be used in the infrared heat bath arrangement as described in the co-pending application filed the same day in the name of the present applicant. In this arrangement, the distal end proximate to the tip 7 is bathed in focused infrared non-laser radiation in a vacuum, allowing precise adjustment of the temperature of the tip up to over 800° C. and even up to 1000° C., and without requiring any active heating components to be situated in the measurement probe 1. In consequence, the mass of the probe 1 and its heat capacity can be kept as low as possible, reducing thermal inertia and permitting the measurement tip to heat up quickly. In the case in which the tip 7 itself is not directly heated by the infrared radiation, it is heated by conduction from the heated part of the probe 1 proximate to the tip 7, the temperature of the tip being measured by thermocouple 25.

As the tip 7 heats up, heat is conducted and radiated in all directions. However, thermal transmission to the proximal end of the measurement probe 1 must be minimised, so as to minimise thermal expansion of the measurement probe 1 and to minimise heat transmitted to the test apparatus in which the measurement probe 1 is being used, and thereby to protect the sensitive electronics contained therein.

The measurement probe 1 of the invention proposes two strategies to minimise heat transmission to the test apparatus, which may be applied either independently, or in combination as in the illustrated embodiment. These strategies go above and beyond the standard solution of merely using thermally insulating materials in the construction of the measurement probe 1, as is done in the prior art.

The first of these strategies involves bead 31. When the distal extremity of the measurement probe 1 is heated up, infrared radiation is emitted in all directions by the heated tip 7, including on the inside of distal element 11. If the bead 31 is metallic-plated, it serves to reflect much of this infrared radiation back towards the interior surfaces of distal element 11 where it is partially re-reflected and partially reabsorbed. Furthermore, the infrared radiation which is not reflected by the bead 31 is absorbed thereby. If the bead 31 is not coated, it will simply absorb most of the infrared radiation impinging thereupon, reducing conduction towards the proximal element.

Since bead 31 is in point contact with core 17, the surface area of the contact between the bead 31 and the core 17 is minimised, and as a result conduction of heat from the former to the latter is equally minimised. Furthermore, the same condition applies to contact between the cylindrical inner wall of distal element 11 and the bead 31. In effect, the maximum theoretical possible contact between the bead 31 and cylindrical inner wall of distal element 11 is a line contact around the circumference of bead 31, however with realistic tolerances this will equally be a point contact, thus minimising thermal conduction from the distal element 11 to the bead 31.

The bead 31 therefore acts effectively as a resistance to infrared radiation generated by the hot distal extremity of the measurement probe 1, to minimise heating of the remainder of the measurement probe 1 by this infrared radiation passing up the inside of the probe 1 and being absorbed by the other components thereof.

This arrangement also permits minimising the amount of metal, e.g. molybdenum, present in the probe body 3, and also its cross-sectional area, thereby minimising heat conduction towards the proximal end of the probe 1.

The second strategy involves the thermal dissipation element 13 and spacers 15 (if present), which serve to minimise transmission of heat from distal element 11 to proximal element 9 via their respective faces.

Figure 3:
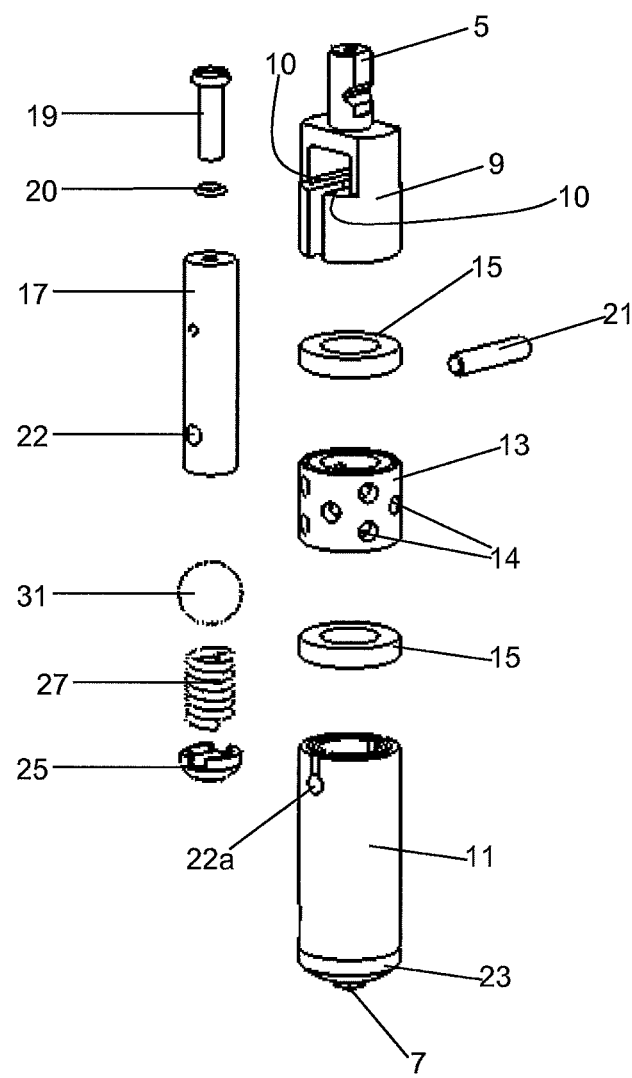
FIG. 3 shows an exploded view of a variant of a probe according to the invention.

In the embodiments of FIGS. 1 to 3, spacers 15 are typically formed as quartz rings situated between each of the proximal element 9 and the distal element 11, and thermal dissipation element 13, however as mentioned above, it is possible to use only one spacer 15, or indeed no spacers 15 (see the embodiment of FIG. 4). Naturally, other material such as glass, alumina, ceramics and so on are also possible. Thermal dissipation element 13 is constructed of a material which absorbs and re-radiates infrared radiation, such as steel. Advantageously, lateral perforations 14 are provided which acts as a labyrinth and helps to ensure that the emitted infrared rays are emitted in an outward direction and not towards the proximal element 9.

In the case in which the spacers 15 are present and are made of quartz, they present a barrier to thermal conduction, yet are however transparent to infrared radiation being emitted by the distal element 11. As a result, infrared radiation being emitted by the distal element 11 in an axial direction (i.e. towards the proximal element 9) is absorbed by the thermal dissipation element 13, and is then predominantly re-radiated in an outward direction (i.e. with a strong radial component) rather than being transmitted axially towards the proximal element 9. This minimises the transmission of heat from the distal element 11 to the proximal element 9 both by conduction and by radiation. Indeed, the only uninterrupted heat path from the distal element 11 to the proximal element 9 is via pin 21, core 17 and screw 19. The pin 21 and the core 17 are constructed of a highly insulating material such as Macor or another glass, ceramic or glass-ceramic, which in and of itself has a high resistance to transmission of heat.

FIG. 3 illustrates a variant of a measurement probe 1 according to the invention. This variant differs from that of FIGS. 1 and 2 in that the mounting interface 5 and the proximal element 9 are combined in a single piece of thermally-insulating material such as Macor or other glass, ceramic or glass-ceramic, which is slotted diametrically so as to form two opposing shoulders 10. Screw 19 bears via resilient element 20 on these shoulders 10, and the lateral slot is left open on each side. Naturally, a single, radial slot is also possible.

FIG. 4 illustrates another variant of a measurement probe 1 according to the invention, in a cross-sectional view along the axis of transverse pin 21. This variant differs from that of FIGS. 1 and 2 primarily in the nature of the retaining arrangement. More precisely, this variant does not comprise a core 17, which is replaced by a tension spring 18 in the retaining arrangement. This tension spring 18 is a simple helical spring which is attached to the proximal element 9 and/or to the mounting interface 5 by being hooked onto upper transverse pin 6, e.g. in a circumferential groove 21a provided therein or alternatively into a hole provided therethrough, and also onto transverse pin 21 in a similar manner. Bead 31 thus contacts transverse pin 21. In the case illustrated, in which a circumferential groove 21a is provided on transverse pin 21, this contact is at two points either side of the groove. It should also be noted in this embodiment that no spacers 15 are provided, although it goes without saying that one or more spacers 15 may be provided on one or both sides of thermal dissipation element 13. As such, this embodiment does not apply the sandwich structure strategy.

FIG. 5 illustrates yet another variant of a measurement probe 1 according to the invention. In this case, mounting interface 5, proximal element 9, and thermal dissipation element 13 are formed as a single piece, in which a first set of perforations 14a are provided at a downward angle, and a second set of perforations 14b are provided as circumferential slots joining circular holes. The first set of perforations 14a favour re-emission of infrared radiation away from mounting interface 5 and hence away from the headstock in which the surface measurement probe 1 is mounted. In this variant, core 17 is significantly shorter than that of the variants of FIGS. 1 to 3, and is hollow to minimise the cross-sectional area available for conduction of heat. Contact area between transverse pin 21 and core 17 is thus much reduced. The end of screw 19 bears on a yet further transverse pin 20 perpendicular to transverse pin 21, pulling the core 17 upwards. Other appropriate arrangement in proximal element 9 may alternatively be provided. It should also be noted in this embodiment that no spacers 15 are provided, although it goes without saying that one or more spaces 15 may be provided between the thermal dissipation element portion 13 of proximal element 9 and the distal element 11.

FIG. 6 illustrates yet another variant of a measurement probe 1 according to the invention, in cross-sectional view perpendicular to the axis of transverse pin 21. This variant represents the global construction of the variant of FIG. 5 combined with the tension spring 18 of FIG. 4, and clearly shows the manner in which the tension spring 18 hooks onto upper transverse pin 6 and transverse pin 21. It should also be noted again in this embodiment that no spacers 15 are provided, although it goes without saying that one or more spaces 15 may be provided between the thermal dissipation element portion 13 of proximal element 9 and the distal element 11.

In summary, the fundamental global structure of the probe 1 to apply the second heat management strategy (i.e. the thermal dissipation element 13) can be described as follows in its major variants. The probe 1 comprises at least two structural elements, one proximal 9, one distal 11, mounted together by a retaining arrangement. The distal element 11 carries the probe tip 7. In the case that only two structural elements are provided, the proximal element 9 integrally incorporates also a thermal dissipation element 13 (see FIGS. 5 and 6, where the thermal dissipation element 13 is formed as one piece with the proximal element 9). In the case in which a separate thermal dissipation element 13 is provided, it is interposed between the proximal element 9 and the distal element 11. In this latter case, a number of spacers 15 may be provided between the thermal dissipation element 13 and one or more of the proximal element 9 and/or distal element 11: FIG. 4 illustrates no spacers 15, and FIGS. 1-3 illustrate two spacers 15, one on each side of the thermal dissipation element 13. It is clear that one (or both) of the spacers 15 of FIGS. 1-3 can be omitted.

Although it is possible to maintain a constant, steady-state temperature difference between the distal end of the proximal end of the measurement probe 1 when in use and the distal end is being heated and the proximal end is being cooled, there is no absolute requirement to do so: it is sufficient that the temperature difference and/or the absolute temperature of the proximal end be maintained within reasonable bounds during the duration of an indentation test, which may only be of the order of several seconds to several minutes.

Although the invention has been described in reference to specific embodiments, these are not to be construed as limiting the scope of the invention as defined in the appended claims.

The invention claimed is:

1. Surface measurement probe comprising:
   a hollow probe body extending along a longitudinal axis and comprising a proximal end adapted to be mounted to a test apparatus and a distal end;
   a retaining arrangement situated inside the probe body and extending along said longitudinal axis, the retaining arrangement being arranged to maintain the surface measurement probe in an assembled state;
   a probe tip supported at the distal end of the probe body and arranged to contact a sample;
   a bead situated inside the probe body and interposed between the probe tip and the retaining arrangement, the bead comprising a thermally-insulating material.

2. Surface measurement probe according to claim 1, wherein the bead comprises a material having a thermal conductivity less than 20 $Wm^{-1}k^{-1}$.

3. Surface measurement probe according to claim 1, wherein the bead comprises a metallic coating, said metallic coating comprising at least one metal selected from the group consisting of gold, silver, aluminium, platinum, rhodium, ruthenium, and palladium.

4. Surface measurement probe according to claim 1, wherein the bead is substantially spherical.

5. Surface measurement probe according to claim 1, wherein said retaining arrangement comprises a transverse pin secured to the distal element, and one of:
   a core maintained in tension, said transverse pin passing through a transverse hole in said core, and said bead being in contact with said core;
   a tension spring attached to said transverse pin, said bead being in contact with said transverse pin.

6. Surface measurement probe according to claim 1, further comprising a bead positioning spring situated between the bead and the probe tip, the bead positioning spring being arranged to act so as to position the bead against a corresponding part of the retaining arrangement.

7. Surface measurement probe according to claim 6, further comprising a thermocouple situated in thermal contact with the probe tip and positioned by said bead positioning spring, a button element optionally being situated between the thermocouple and the bead positioning spring.

8. Surface measurement probe according to claim 1, wherein the bead comprises a material having a thermal conductivity less than 10 $Wm^{-1}k^{-1}$.

9. Surface measurement probe comprising:
   a tubular probe body extending along a longitudinal axis and comprising a proximal end adapted to be mounted to a test apparatus and a distal end;
   a retaining arrangement situated inside the probe body and extending along said longitudinal axis, the retaining arrangement being arranged to maintain the surface measurement probe in an assembled state;
   a probe tip supported at the distal end of the probe body and arranged to contact a sample; wherein the probe body comprises a distal element situated at said distal end, a proximal element situated at said proximal end, and a thermal dissipation element sandwiched between said distal element and said proximal element.

10. Surface measurement probe according to claim 9, wherein the thermal dissipation element is separated from at least one of the proximal element and the distal element by a respective spacer comprising a thermally-insulating material.

11. Surface measurement probe according to claim 10, wherein said spacer comprises a material having a thermal conductivity of less than 20 $Wm^{-1}k^{-1}$.

12. Surface measurement probe according to claim 11, wherein said material comprised by said spacer that has a thermal conductivity of less than 20 $Wm^{-1}k^{-1}$ is quartz.

13. Surface measurement probe according to claim 11, wherein the bead comprises a material having a thermal conductivity less than 10 $Wm^{-1}k^{-1}$.

14. Surface measurement probe according to claim 10, wherein the thermal dissipation element is integral with the proximal element.

15. Surface measurement probe according to claim 9, wherein the retaining arrangement extends through at least part of the proximal element, the spacer, the thermal dissipation element and part of the distal element.

16. Surface measurement probe according to claim 9, wherein the retaining arrangement comprises a transverse pin secured to the distal element.

17. Surface measurement probe according to claim 16, wherein the retaining arrangement comprises a core through which passes said transverse pin, the core being secured to the proximal element by a screw passing through a hole provided in the proximal element such that the core is maintained in tension.

18. Surface measurement probe according to claim 17, wherein the core is of a thermally insulating material having a thermal conductivity of less than 20 $Wm^{-1}k^{-1}$.

19. Surface measurement probe according to claim 18, wherein the bead comprises a material having a thermal conductivity less than 10 $Wm^{-1}k^{-1}$.

20. Surface measurement probe according to claim 16, wherein the retaining arrangement comprises a tension spring attached to said transverse pin and to said proximal element.

* * * * *